(12) United States Patent
Toida

(10) Patent No.: US 6,542,246 B1
(45) Date of Patent: Apr. 1, 2003

(54) BLOOD VESSEL IMAGING SYSTEM

(75) Inventor: Masahiro Toida, Kaisei-machi (JP)

(73) Assignee: Fuji Photo Film Co., Ltd., Kanagawa (JP)

(*) Notice: Subject to any disclaimer, the term of this patent is extended or adjusted under 35 U.S.C. 154(b) by 0 days.

(21) Appl. No.: 09/496,283

(22) Filed: Feb. 1, 2000

Related U.S. Application Data (63) Continuation-in-part of application No. 09/444,380, filed on Nov. 22, 1999, now abandoned.

(30) Foreign Application Priority Data

Nov. 20, 1998 (JP) .......................................... 10-331410
Nov. 20, 1998 (JP) .......................................... 10-331411
Nov. 19, 1999 (JP) .......................................... 11-329361

(51) Int. Cl.$^7$ ................................................ G01B 9/02
(52) U.S. Cl. ...................................... 356/484; 600/310
(58) Field of Search ............................. 356/484–485; 600/504

(56) References Cited

U.S. PATENT DOCUMENTS 4,976,268 A * 12/1990 Kurosawa et al. .......... 128/687

6,374,128 B1 * 4/2002 Toida et al. ................. 600/310

OTHER PUBLICATIONS

Japanese ME Academy Magazine BME, vol. 8, No. 5, pp. 41–50, 1994.

* cited by examiner

Primary Examiner—Frank G. Font
Assistant Examiner—Phil Natividad
(74) Attorney, Agent, or Firm—Sughrue Mion, PLLC (57) ABSTRACT

A blood vessel imaging system includes a measuring light source which emits a measuring light beam. An optical heterodyne detection system consists of an optical system which splits the measuring light beam into a first light beam traveling to impinge upon an organism and a second light beam traveling not to impinge upon the organism and combines the second light beam with the first beam emanating from the organism into a combined light beam, a frequency shifter which causes the first and second light beams to have frequencies different from each other, and a beat component detector which detects beat components of the combined light beam. An image signal is generated on the basis of the ratio of the intensity of a pulsation wave band signal to the intensity of a beat signal included in an output signal of the optical heterodyne detection system.

26 Claims, 6 Drawing Sheets

BLOOD VESSEL IMAGING SYSTEM

This application is a continuation-in-part application of application Ser. No. 09/444,380 filed Nov. 22, 1999, now abandoned.

BACKGROUND OF THE INVENTION

1. Field of the Invention

This invention relates to a blood vessel imaging system for imaging blood vessels, and more particularly to a blood vessel imaging system which can image blood vessels with arteries and veins distinguished from each other. This invention also relates to a method and system for determining a spatial distribution of a pulsation wave signal representing a pulsation wave of an artery of an organism.

2. Description of the Related Art

In the clinical field, there has been a wide demand for imaging arteries and veins clearly distinguished from each other. For example, since arteriosclerosis generally starts at the periphery of the arteries, it will be useful in diagnosing arteriosclerosis if the inner walls of the peripheral arteries can be imaged distinguished from those of the veins.

There has been wide known angiography as a system for imaging blood vessels. However angiography is disadvantageous in that load on the testee is heavy and the testee generally must stay in the hospital.

Further there has been proposed technique for imaging a part of an organism on the basis of penetration of light through the part as disclosed in "Japanese ME Academy Magazine BME", vol.8, No.5, 1994, pp. 41~50. However it is very difficult to image arteries and veins clearly distinguished from each other by the technique.

Also, as a technique for extracting information representing a pulsation wave of an artery, a technique has heretofore been known, in which measuring light beams having two different wavelengths are irradiated to an organism, a logarithm of pulsation wave amplitude is calculated from each of detection signals obtained by detecting the measuring light beams having passed through the organism, and thereafter pulsation wave components are calculated in accordance with the ratio of the two logarithms to each other. However, with this technique for directly detecting the measuring light beams, it is impossible to determine a spatial distribution of a pulsation wave signal representing pulsation wave information.

SUMMARY OF THE INVENTION

In view of the foregoing observations and description, the primary object of the present invention is to provide a blood vessel imaging system which can image blood vessels with arteries and veins clearly distinguished from each other without exposing the testee to heavy load.

Another object of the present invention is to provide a method of determining a spatial distribution of a pulsation wave signal, wherein a spatial distribution of a pulsation wave signal representing a pulsation wave of an artery of an organism is capable of being determined.

The specific object of the present invention is to provide a system for carrying out the method of determining a spatial distribution of a pulsation wave signal.

In blood vessel imaging systems in accordance with one aspect of the present invention, an optical heterodyne detection system is employed in order to ensure high spatial resolution to an organism as a scattering medium, and arteries and veins are distinguished from each other on the basis of the fact that the output signal of the heterodyne detection system is modulated by the pulsation wave unique to arteries when the measuring light beam is projected onto an artery.

That is, in accordance with a first aspect of the present invention, there is provided a blood vessel imaging system comprising a measuring light source which emits a measuring light beam, a scanning means which causes the measuring light beam to scan an organism, an optical heterodyne detection system consisting of an optical system which splits the measuring light beam upstream of the organism into a first light beam traveling to impinge upon the organism and a second light beam traveling not to impinge upon the organism and combines the second light beam with the first beam emanating from the organism into a combined light beam, a frequency shifter which causes the first and second light beams to have frequencies different from each other, and a beat component detecting means which detects beat components of the combined light beam, and an image signal generating means which generates an image signal on the basis of the ratio of the intensity of a pulsation wave band signal to the intensity of a beat signal included in an output signal of the optical heterodyne detection system.

It is preferred that the blood vessel imaging system be further provided with a frequency analysis means which analyzes the output signal of the optical heterodyne detection system, and the image signal generating means obtains the intensity ratio on the basis of the pulsation wave band signal and the beat signal separated from each other by the frequency analysis means on a frequency axis.

It is preferred that the image signal generating means generates an image signal representing artery parts of the organism when the intensity ratio is higher than a predetermined threshold level.

A blood vessel imaging system in accordance with a second embodiment of the present invention comprises a measuring light source, a scanning means and an optical heterodyne detection system similar to those in the blood vessel imaging system of the first aspect and is further provided with an image signal generating means which generates an image signal on the basis of the degree of modulation at a pulsation wave band frequency of a beat signal included in an output signal of the optical heterodyne detection system.

In the blood vessel imaging system in accordance with the second aspect, it is preferred that a pulsation wave detecting means which detects a pulsation wave of the organism be provided, and the image signal generating means samples the signal value when the beat signal is in a predetermined phase on the basis of an output signal of the pulsation wave detecting means.

Further it is preferred that the image signal generating means generates an image signal representing artery parts of the organism when the degree of modulation is higher than a predetermined threshold level.

Further it is preferred in the blood vessel imaging systems in accordance with both the first and second aspects of the present invention that the measuring light source comprises a linear or two-dimensional array of a plurality of light emitting portions, and the optical heterodyne detection system is arranged to be able to detect in parallel beat components of the combined light beams based on the measuring light beams from the respective light emitting portions, and the measuring light source and the optical heterodyne detection system also function as at least a part of said scanning means.

The beat component detection signal (beat signal) output from the heterodyne detection system described above represents intensity of only straight light components traveling straight through the organism or scattered light components close to the straight light components except influence of scattering by the organism which is a scattering medium.

Figure 5:
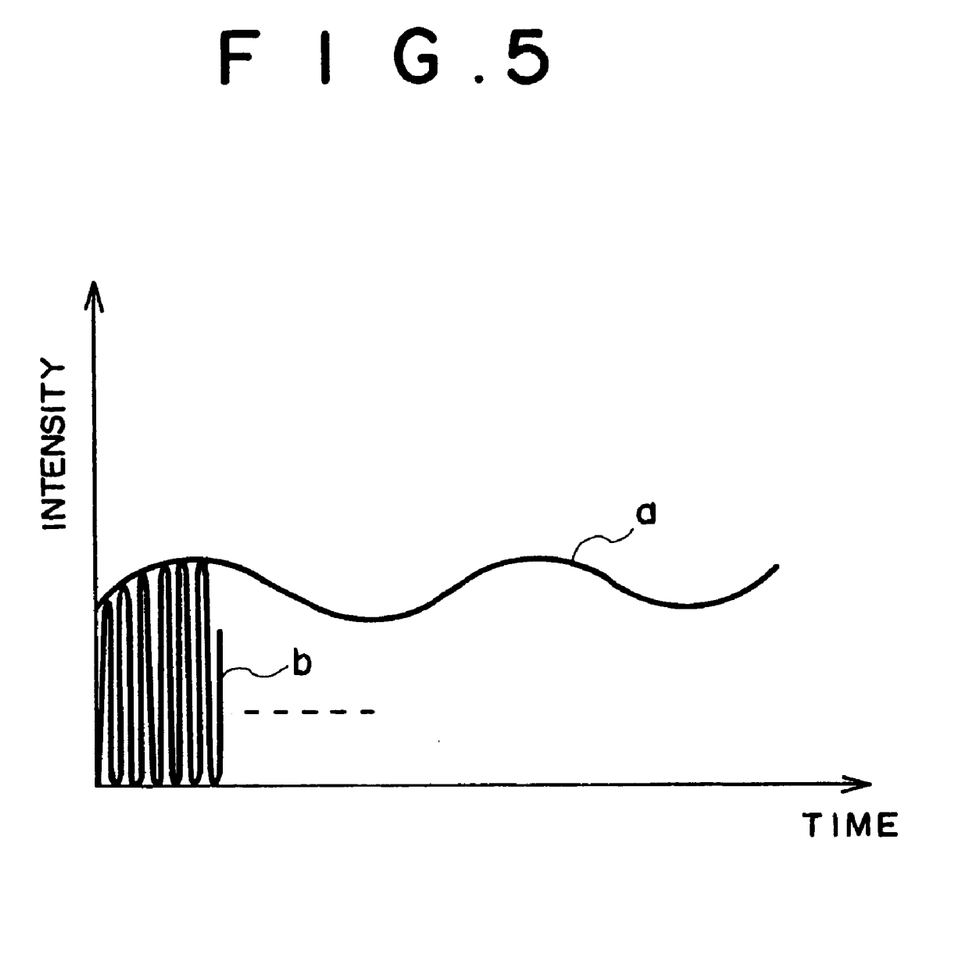
FIG. 5 is a view for illustrating modulation of the beat signal by the pulsation wave.

The artery part and the vein part are distinguished from each other in the following manner. While the first light beam split from the measuring light beam as emitted from the light source is being projected onto an artery part, the output signal of the optical heterodyne detection system consists of a pulsation wave signal a at a frequency of about 1 Hz generated by pulsation of the artery and a beat signal b superimposed one on the other as shown in FIG. 5. While the first light beam is being projected onto a vein part, there is generated no pulsation wave signal.

Figure 2:
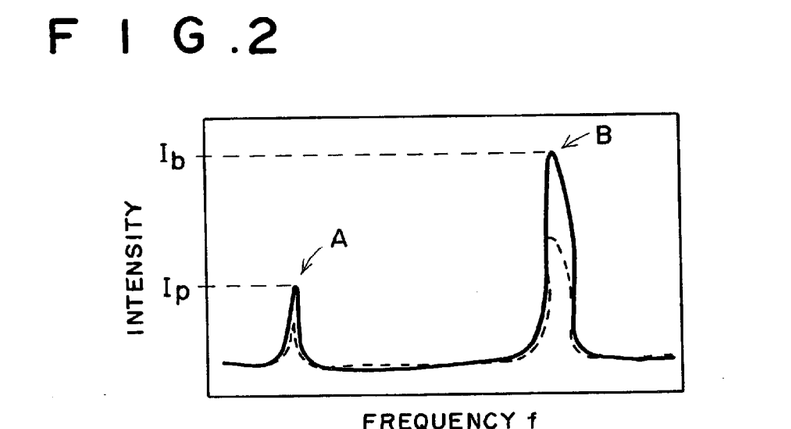
FIG. 2 is a view showing a spectrum of the output of the photodetector in the blood vessel imaging system of the first embodiment.

When the output signal which varies with time as shown in FIG. 5 is sampled at a certain timing and subjected to frequency analysis, a spectrum such as shown in FIG. 2 is obtained. In FIG. 2, the pulsation wave signal component is indicated at A and the beat signal component is indicated at B. The intensities of the pulsation wave signal and the beat signal vary in response to the pulsation as shown by the solid line and the broken line in FIG. 2 and with attenuation of the first light beam due to absorption and/or scattering by the organism.

Though the intensities of the pulsation wave signal and the beat signal vary, the ratio of the intensity of the former to that of the latter is kept unchanged. Accordingly when the intensity ratio is higher than a certain level, it may be considered that a pulsation wave signal is being generated, that is, the first light beam is being projected onto an artery part. When the output signal of the optical heterodyne detection system is space-divided as the measuring light beam (the first light beam) scans the organism and an image signal component is generated for each scanning spot, the artery part can be imaged on the basis of an image signal made up of a plurality of image signal components thus obtained.

For example, when the image signal generating means generates an image signal component bearing thereon a relatively high density (low brightness) when the intensity ratio is higher than a predetermined threshold value and generates an image signal component bearing thereon a relatively low density (high brightness) when the intensity ratio is not higher than the threshold value, an image in which the artery part is shown as a relatively high density part on a background at a relatively low density can be obtained.

When the image signal generating means is arranged to generate an image signal component bearing thereon a density which becomes higher as the intensity ratio increases, an image in which the artery part can be clearly distinguished from other parts as a relatively high density part can also be obtained.

Figure 4:
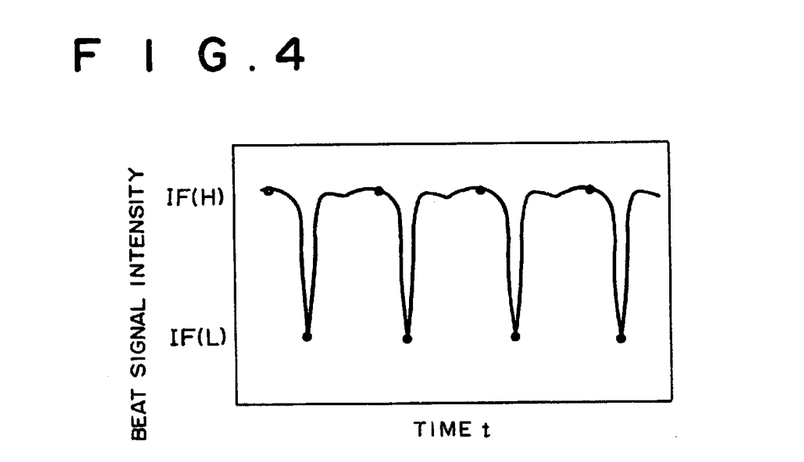
FIG. 4 is a view showing change in intensity of the beat signal obtained in the blood vessel imaging system of the second embodiment.

When the beat signal b is extracted, for instance, by passing a signal, whose waveform is as shown in FIG. 5, through a band-pass filter, change with time of the intensity of the extracted beat signal b is as shown in FIG. 4. As shown in FIG. 4, the intensity of the beat signal b periodically changes since the beat signal b is modulated by the pulsation signal.

The degree of modulation of the beat signal b represented by formula $\{IF(H)-IF(L)\}/\{IF(H)+IF(L)\}$, wherein $IF(H)$ represents the peak intensity of the beat signal b and $IF(L)$ represents the bottom intensity of the same, is basically kept unchanged even if the intensities of the pulsation wave signal and the beat signal vary with attenuation of the first light beam due to absorption and/or scattering by the organism. Accordingly when the degree of modulation is higher than a certain level, it may be considered that the first light beam is being projected onto an artery part.

When the output signal of the optical heterodyne detection system is space-divided as the measuring light beam (the first light beam) scans the organism and an image signal component is generated for each scanning spot, the artery part can be imaged on the basis of an image signal made up of a plurality of image signal components thus obtained.

For example, when the image signal generating means generates an image signal component bearing thereon a relatively high density (low brightness) when the degree of modulation is higher than a predetermined threshold value and generates an image signal component bearing thereon a relatively low density (high brightness) when the degree of modulation is not higher than the threshold value, an image in which the artery part is shown as a relatively high density part on a background at a relatively low density can be obtained.

When the image signal generating means is arranged to generate an image signal component bearing thereon a density which becomes higher as the degree of modulation increases, an image in which the artery part can be clearly distinguished from other parts as a relatively high density part can also be obtained.

When there is provided a pulsation wave detecting means which detects a pulsation wave of the organism, and the image signal generating means samples the signal value when the beat signal is in a predetermined phase on the basis of an output signal of the pulsation wave detecting means, it is possible to accurately sample the peak intensity $IF(H)$ and the bottom intensity $IF(L)$ of the beat signal 6, whereby an accurate value of the degree of modulation can be constantly obtained.

Further when a measuring light source comprising a linear or two-dimensional array of a plurality of light emitting portions and an optical heterodyne detection system which can detect in parallel beat components of the combined light beams based on the measuring light beams from the respective light emitting portions are employed so that the measuring light source and the optical heterodyne detection system also function as at least a part of said scanning means, it becomes unnecessary for the scanning means to mechanically cause the measuring light beam to scan the organism in at least one direction, whereby the scanning speed, which results in the imaging speed, can be increased.

This is especially advantageous in the case where the image signal generating means samples the signal value when the beat signal is in a predetermined phase and sampling of the signal requires a relatively long time.

In blood vessel imaging systems in accordance with another aspect of the present invention, a pair of optical heterodyne detection systems which are different in frequency of measuring light beam are employed in order to ensure high spatial resolution to an organism as a scattering medium, the degree of oxygen saturation of the part of the organism onto which the measuring light beams are projected is determined on the basis of the output signals of the optical heterodyne detection systems, and arteries and veins are distinguished from each other on the basis of the fact that the degree of oxygen saturation is higher in arteries than in veins.

In accordance with a third aspect of the present invention, there is provided a blood vessel imaging system comprising

- a measuring light source which emits first and second measuring light beams which are different in frequency,
- an incident optical system which causes the first and second measuring light beams to impinge upon the organism in the same position,
- a scanning means which causes the first and second measuring light beams to scan an organism,
- a first optical heterodyne detection system consisting of an optical system which splits the first measuring light beam upstream of the organism into a first section traveling to impinge upon the organism and a second section traveling not to impinge upon the organism and combines the second section with the first section emanating from the organism into a first combined light beam, a frequency shifter which causes the first and second sections of the first light beam to have frequencies different from each other, and a beat component detecting means which detects beat components of the first combined light beam,
- a second optical heterodyne detection system consisting of an optical system which splits the second measuring light beam upstream of the organism into a first section traveling to impinge upon the organism and a second section traveling not to impinge upon the organism and combines the second section with the first section emanating from the organism into a second combined light beam, a frequency shifter which causes the first and second sections of the second light beam to have frequencies different from each other, and a beat component detecting means which detects beat components of the second combined light beam, and
- an image signal generating means which calculates characteristic value in one-to-one correspondence to a degree of oxygen saturation on the basis of beat component detection signals respectively output from the first and second optical heterodyne detection systems, and generates an image signal on the basis of the characteristic value.

In this specification, the characteristic value may be the degree of oxygen saturation itself.

For example, the image signal generating means may generate an image signal employing, as the characteristic value, the ratio between a logarithm of amplitude of the beat component detection signal output from the first optical heterodyne detection system due to a pulsation wave of the organism and a logarithm of amplitude of the beat component detection signal output from the second optical heterodyne detection system due to the pulsation wave of the organism.

In the case where the image signal is generated on the basis of the ratio of the logarithms of the amplitudes, for instance, there are provided a filtering means which extracts modulated components at frequencies in the pulsation wave bands out of the beat component detection signals respectively output from the first and second optical heterodyne detection systems, and a level meter which measures levels of the signals extracted by the filtering means, and the image signal generating means obtains the amplitudes due to the pulsation wave on the basis of output signals of the level meter.

Otherwise, a pulsation wave detecting means which detects a pulsation wave output from the organism and a sampling means which samples the beat component detection signals respectively output from the first and second optical heterodyne detection systems at timings at which the beat component detection signals are maximized and minimized on the basis of an output signal of the pulsation wave detecting means may be provided, and the image signal generating means may obtain the amplitudes due to the pulsation wave on the basis of the sampled values of beat components detection signals.

It is preferred that the first and second measuring light beams respectively be 760 nm and 930 nm in frequency.

Further it is preferred that the image signal generating means outputs an image signal representing an artery part of the organism when it calculates said characteristic value to be a value corresponding to a degree of oxygen saturation of 80 to 90%.

Further it is preferred in the blood vessel imaging system in accordance with the third aspect of the present invention that the measuring light source comprises first and second linear or two-dimensional arrays of a plurality of light emitting portions, the light emitting portions of the first array emitting a plurality of first measuring light beams and the light emitting portions of the second array emitting a plurality of second measuring light beams, the first optical heterodyne detection system is arranged to be able to detect in parallel beat components of the first combined light beams based on the first measuring light beams from the respective light emitting portions, the second optical heterodyne detection system is arranged to be able to detect in parallel beat components of the second combined light beams based on the second measuring light beams from the respective light emitting portions, and the measuring light source and the optical heterodyne detection systems also function as at least a part of said scanning means.

The beat component detection signal (beat signal) output from each of the first and second heterodyne detection systems described above represents intensity of only straight light components traveling straight through the organism or scattered light components close to the straight light components except influence of scattering by the organism which is a scattering medium. The beat signals are modulated at a frequency of about 1 Hz by the pulsation wave of the organism when the first and second measuring light beams are being projected onto an artery part of the organism.

By using the first and second measuring light beams which are different in frequency and calculating, for instance, the ratio between a logarithm of amplitude of the beat component detection signal output from the first optical heterodyne detection system due to a pulsation wave of the organism and a logarithm of amplitude of the beat component detection signal output from the second optical heterodyne detection system due to the pulsation wave of the organism, the degree of oxygen saturation of blood in the part of the organism exposed to the measuring light beams can be obtained. Since the degree of oxygen saturation of arterial blood is 80 to 90%, an image in which the artery part can be clearly distinguished from vein parts and other can be obtained by generating an image signal representing artery parts when a degree of oxygen saturation of 80 to 90% is detected.

The intensity of the beat signal with attenuation of the measuring light beam due to absorption and/or scattering by a tissue of the organism and the attenuation of the measuring light beam changes with the thickness of the tissue and the like. Though the intensities of the beat signals vary, the aforesaid ratio of the logarithms is constantly in one-to-one correspondence to the degree of oxygen saturation with the change in the intensities of the beat signals compensated for, whereby the artery parts can be accurately imaged.

For example, when the image signal generating means generates an image signal component bearing thereon a relatively high density (low brightness) when the degree of oxygen saturation represented by the characteristic value is 80 to 90% and generates an image signal component bearing thereon a relatively low density (high brightness) when the degree of oxygen saturation is lower than 80%, an image in which the artery part is shown as a relatively high density part on a background at a relatively low density can be obtained.

Further when a measuring light source comprising first and second linear or two-dimensional arrays of a plurality of light emitting portions, the light emitting portions of the first array emitting a plurality of first measuring light beams and the light emitting portions of the second array emitting a plurality of second measuring light beams, a first optical heterodyne detection system arranged to be able to detect in parallel beat components of the first combined light beams based on the first measuring light beams from the respective light emitting portions, and a second optical heterodyne detection system arranged to be able to detect in parallel beat components of the second combined light beams based on the second measuring light beams from the respective light emitting portions are employed so that the measuring light source and the optical heterodyne detection systems also function as at least a part of said scanning means, it becomes unnecessary for the scanning means to mechanically cause the measuring light beam to scan the organism in at least one direction, whereby the scanning speed, which results in the imaging speed, can be increased.

This is especially advantageous in the case where the image signal generating means obtains the characteristic value from the values of the beat signals when the beat signals are in a predetermined phase on the basis of the output signal of the pulsation wave detecting means and, accordingly, sampling of the signal requires a relatively long time.

In accordance with a fourth aspect of the present invention, there is provided a system for determining a spatial distribution of a pulsation wave signal, comprising

- a measuring light source which emits a measuring light beam impinging upon an organism,
- an optical heterodyne detection system consisting of an optical system which splits the measuring light beam upstream of the organism into a first light beam traveling to impinge upon the organism and a second light beam traveling not to impinge upon the organism and combines the second light beam with the first beam emanating from the organism into a combined light beam, a frequency shifter which causes the first and second light beams to have frequencies different from each other, and a beat component detecting means which detects beat components of the combined light beam, and
- a pulsation wave signal generating means for generating a pulsation wave signal, which represents a pulsation wave of the organism, on the basis of an output signal of the optical heterodyne detection system.

By way of example, the pulsation wave signal generating means may be a means, which generates the pulsation wave signal on the basis of the ratio of the intensity of a pulsation wave band signal to the intensity of a beat signal included in the output signal of the optical heterodyne detection system. In such cases, it is preferred that the pulsation wave signal generating means generates a pulsation wave signal, which represents a pulsation wave of an artery of the organism, when the intensity ratio is higher than a predetermined threshold level.

Alternatively, the pulsation wave signal generating means may be a means, which generates the pulsation wave signal on the basis of the degree of modulation at a pulsation wave band frequency of the beat signal included in the output signal of the optical heterodyne detection system. In such cases, it is preferred that the pulsation wave signal generating means generates a pulsation wave signal representing a pulsation wave of an artery of the organism when the degree of modulation is higher than a predetermined threshold level.

In accordance with a fifth aspect of the present invention, there is provided a system for determining a spatial distribution of a pulsation wave signal, comprising

- a measuring light source which emits first and second measuring light beams which are different in frequency,
- an incident optical system which causes the first and second measuring light beams to impinge upon the organism in the same position,
- a scanning means which causes the first and second measuring light beams to scan an organism,
- a first optical heterodyne detection system consisting of an optical system which splits the first measuring light beam upstream-of the organism into a first section traveling to impinge upon the organism and a second section traveling not to impinge upon the organism and combines the second section with the first section emanating from the organism into a first combined light beam, a frequency shifter which causes the first and second sections of the first light beam to have frequencies different from each other, and a beat component detecting means which detects beat components of the first combined light beam,
- a second optical heterodyne detection system consisting of an optical system which splits the second measuring light beam upstream of the organism into a first section traveling to impinge upon the organism and a second section traveling not to impinge upon the organism and combines the second section with the first section emanating from the organism into a second combined light beam, a frequency shifter which causes the first and second sections of the second light beam to have frequencies different from each other, and a beat component detecting means which detects beat components of the second combined light beam, and
- a pulsation wave signal generating means which calculates characteristic value in one-to-one correspondence to a degree of oxygen saturation on the basis of beat component detection signals respectively output from the first and second optical heterodyne detection systems, and generates a pulsation wave signal on the basis of the characteristic value.

In the system for determining a spatial distribution of a pulsation wave signal in accordance with the fifth aspect of the present invention, the pulsation wave signal generating means should preferably generate the pulsation wave signal by employing, as the characteristic value, the ratio between a logarithm of amplitude of the beat component detection signal output from the first optical heterodyne detection system due to a pulsation wave of the organism and a logarithm of amplitude of the beat component detection signal output from the second optical heterodyne detection system due to the pulsation wave of the organism.

Also, in the system for determining a spatial distribution of a pulsation wave signal in accordance with the fifth aspect of the present invention, a wavelength $\lambda 1$ of the first measuring light beam should preferably fall within the range of 600 nm<$\lambda 1$<805 nm, and a wavelength $\lambda 2$ of the second measuring light beam should preferably fall within the range of 805 nm<$\lambda 2$<1,100 nm. The wavelength $\lambda 1$ of the first measuring light beam should more preferably be 760 nm, and the wavelength $\lambda 2$ of the second measuring light beam should more preferably be 930 nm.

The present invention further provides a method of determining a spatial distribution of a pulsation wave signal, comprising the steps of obtaining a pulsation wave signal by utilizing the system for determining a spatial distribution of a pulsation wave signal in accordance with the fourth or fifth aspect of the present invention, i.e. the system utilizing the optical heterodyne detection system.

With the systems for determining a spatial distribution of a pulsation wave signal in accordance with the present invention, wherein the pulsation wave signal is obtained by utilizing the optical heterodyne detection technique, basically, the pulsation wave signal corresponding to only the part, upon which the measuring light beam impinges, can be obtained. Therefore, the spatial distribution of the pulsation wave signal concerning the organism can be determined by obtaining pulsation wave signals corresponding to two or more different points on the organism by use of the system for determining a spatial distribution of a pulsation wave signal.

DESCRIPTION OF THE PREFERRED EMBODIMENTS

Figure 1:
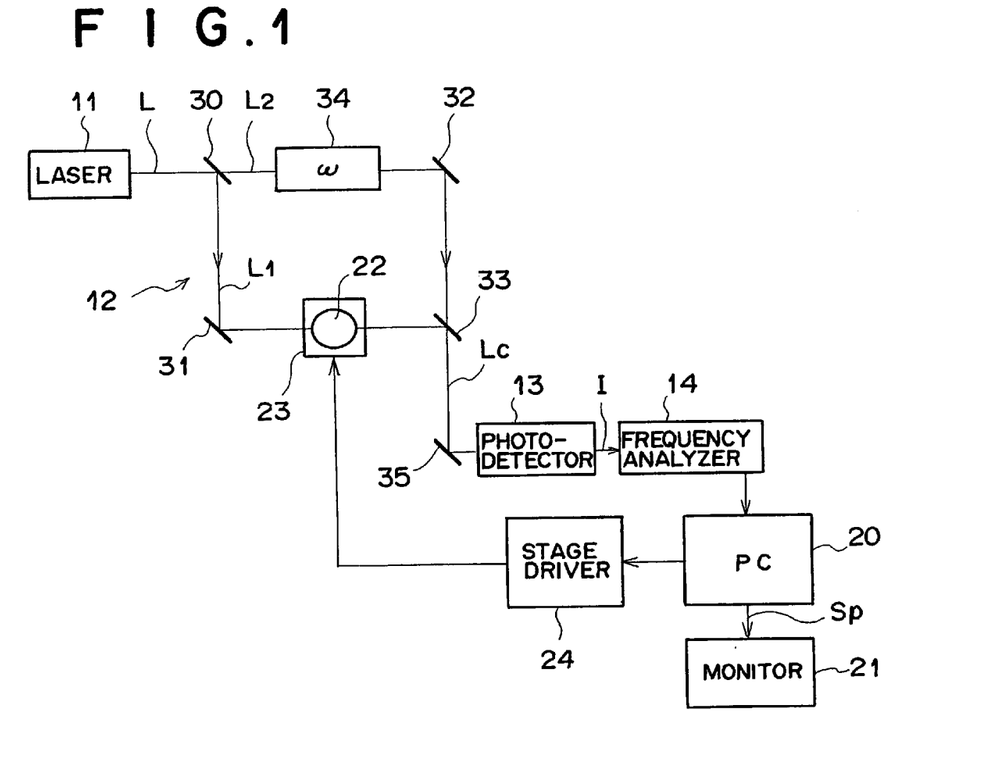
FIG. 1 is a schematic view showing a blood vessel imaging system in accordance with a first embodiment of the present invention.

In FIG. 1, a blood vessel imaging system in accordance with a first embodiment of the present invention comprises a laser 11 emitting a measuring light beam L at a wavelength of $\lambda$, a light heterodyne optical system 12, a photodetector 13 which receives the measuring light beam L emanating from the light heterodyne optical system 12, and a frequency analyzer 14 connected to the photodetector 13.

The imaging system further comprises a personal computer (PC) 20 which receives output of the frequency analyzer 14 and forms an image signal generating means together with the frequency analyzer 14, and an image monitor 21 such as a CRT display connected to the personal computer 20.

Further, there is provided a X-Y stage 23 which is movable in X and Y directions supporting thereon an object (e.g., a human finger) 22. A stage driver 24 drives the X-Y stage 23 under the control of the personal computer 20.

The optical system 12 and the photodetector 13 form an optical heterodyne detection system. The optical system 12 comprises a first half-silvered mirror 30 which splits the measuring light beam L into a first light beam L1 (the part of the measuring light beam L reflected by the first half-silvered mirror 30) and a second light beam L2 (the part of the measuring light beam L passing through the first half-silvered mirror 30), a first mirror 31 which reflects the first light beam L1 to impinge upon the object 22, a second mirror 32 which reflects the second light beam L2, a second half-silvered mirror 33 which combines the first light beam L1 passing through the object 22 with the second light beam L2 reflected from the second mirror 32 into a combined light beam Lc, and a third mirror 35 which reflects the combined light beam Lc to impinge upon the photodetector 13.

A frequency shifter 34 provided on the optical path of the second light beam L2 shifts the second light beam L2 by a predetermined amount so that the center frequency of the second light beam L2 becomes $\omega$. The frequency shifter 34 may comprise, for instance, an AOM.

Operation of the blood vessel imaging system of this embodiment will be described, hereinbelow. When taking a blood vessel image, a measuring light beam L is emitted from the laser 11 and the first light beam L1 is projected onto the object 22. While projecting the first light beam L1, the X-Y stage 23 is moved in X and Y directions, whereby the first light beam L1 is caused to two-dimensionally scan the object 22.

When the first light beam L1 passing through the object 22 is combined with the frequency-shifted second light beam L2 by the second half-silvered mirror 33 into a combined light beam Lc, the combined light beam Lc includes therein beat components whose center frequency is $\omega$, equal to that of the frequency-shifted second light beam L2. The output signal I of the photodetector 13 upon receipt of the combined light beam Lc includes a beat signal generated by the beat components. The output signal I of the photodetector 13 is input into the frequency analyzer 14.

The beat signal represents intensity of only straight light components traveling straight through the object 22, which is a scattering medium, or scattered light components close to the straight light components. Accordingly, by obtaining an image signal for the object 22 on the basis of the beat signal, a high spatial resolution can be ensured though the measuring light beam L (the first light beam L1) is scattered by the object 22.

The frequency analyzer 14 obtains a spectrum of the output signal I. The spectrum obtained as shown in FIG. 2. In FIG. 2, the beat signal component is indicated at B. As described above, when the measuring light beam L is being projected onto an artery part, a pulsation wave signal is also generated as indicated at A.

The personal computer 20 receives the output of the frequency analyzer 14, and obtains a peak value Ib of the beat signal component B, whose center frequency is $\omega$, and a peak value Ip of the signal in the pulsation wave band near 1 Hz, thereby obtaining an intensity ratio Ip/Ib. The personal computer 20 generates an image signal component Sp bearing thereon a relatively high density (low brightness)

when the intensity ratio Ip/Ib is higher than a predetermined threshold level and otherwise an image signal component Sp bearing thereon a relatively low density (high brightness), and inputs the image signal component Sp into the monitor 21.

The photodetector 13 outputs the signal I for each scanning spot on the object 22 as the first light beam L1 scans the object 22. Accordingly, the two-valued image signal component Sp is generated for each scanning spot on the object 22.

The image monitor 21 reproduces a two-dimensional image on the basis of an image signal made up of the image signal components Sp thus generated for the respective scanning spots. In the image, only the artery part of the object 22 is shown.

The personal computer 20 may generate an image signal bearing thereon a density which becomes higher as the intensity ratio Ip/Ib increases without processing the intensity ratio Ip/Ib with the threshold value. In this case, the artery part is shown in a density clearly higher than other parts.

Figure 3:
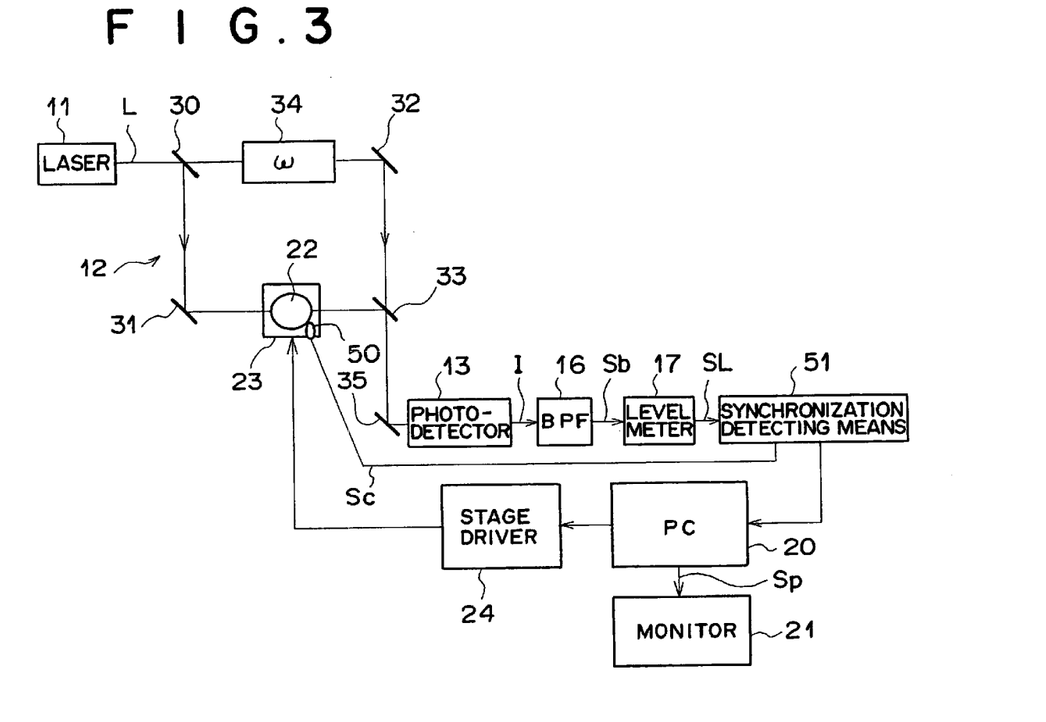
FIG. 3 is a schematic view showing a blood vessel imaging system in accordance with a second embodiment of the present invention.

A blood vessel imaging system in accordance with a second embodiment of the present invention will be described with reference to FIG. 3, hereinbelow. In FIG. 3, the elements analogous to those shown in FIG. 1 are given the same reference numerals and will not be described here.

The blood vessel imaging system of this embodiment basically differs from that of the first embodiment in that there are provided a band-pass filter 16 and a level meter 17 in place of the frequency analyzer 14 and there are further provided a pulsation signal detecting means 50 such as an electrocardiograph which detects a pulsation wave of the object 22, and a synchronization detecting means 51 which samples a level signal SL output from the level meter 17 on the basis of a pulsation signal Sc output from the pulsation signal detecting means 50.

The band-pass filter 16 receives an output signal I of the photodetector 13 and extracts therefrom a beat signal Sb near the center frequency ω. Then the band-pass filter 16 inputs the beat signal Sb into the level meter 17. The level meter 17 measures the intensity of the beat signal Sb and inputs a level signal SL representing the measured intensity of the beat signal Sb into the synchronization detecting means 51. The intensity of the beat signal Sb is as shown in FIG. 4. When the measuring light beam L (the first light beam L1) is being projected onto an artery part, the beat signal Sb is modulated at a frequency of about 1 Hz by the pulsation wave of the organism. When the measuring light beam L (the first light beam L1) is being projected onto a part other than an artery part, such modulation does not occur.

The synchronization detecting means 51 samples the level signal SL at times at which the beat signal Sb takes a peak value and a bottom value as shown by black dots in FIG. 4 on the basis of the pulsation wave signal Sc, and inputs a sampling signal into the personal computer 20. The personal computer 20 obtains a degree of modulation of the beat signal {IF(H)–IF(L)}/{IF(H)+IF(L)}, wherein IF(H) represents the peak intensity of the beat signal b and IF(L) represents the bottom intensity of the same. The personal computer 20 generates an image signal component Sp bearing thereon a relatively high density (low brightness) when the degree of modulation is higher than a predetermined threshold level and otherwise an image signal component Sp bearing thereon a relatively low density (high brightness), and inputs the image signal component Sp into the monitor 21.

The photodetector 13 outputs the signal I for each scanning spot on the object 22 as the first light beam L1 scans the object 22. Accordingly, the two-valued image signal component Sp is generated for each scanning spot on the object 22.

The image monitor 21 reproduces a two-dimensional image on the basis of an image signal made up of the image signal components Sp thus generated for the respective scanning spots. In the image, only the artery part of the object 22 is shown.

The personal computer 20 may generate an image signal bearing thereon a density which becomes higher as the degree of modulation increases without processing the degree of modulation with the threshold value. In this case, the artery part is shown in a density clearly higher than other parts.

Figure 6:
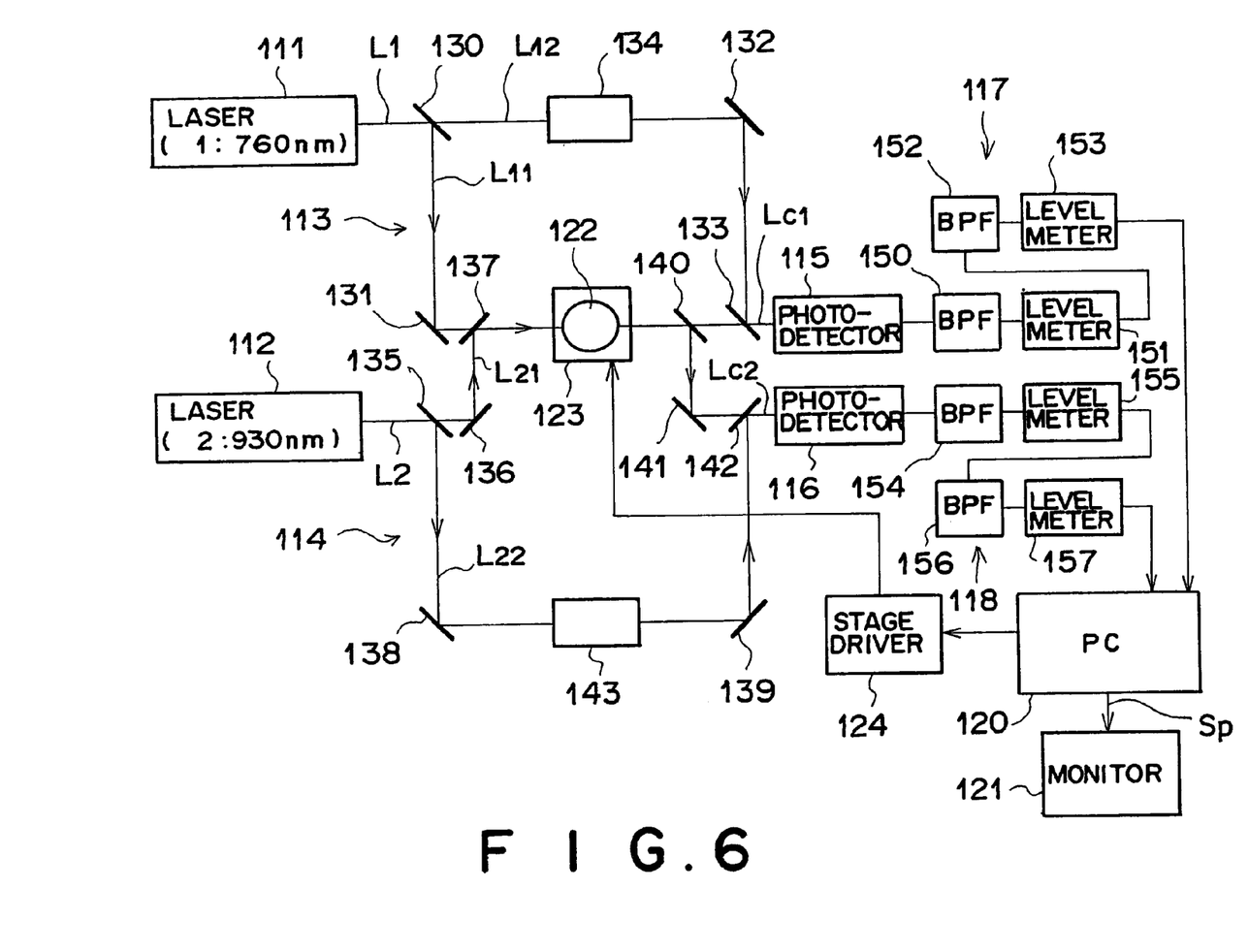
FIG. 6 is a schematic view showing a blood vessel imaging system in accordance with a third embodiment of the present invention.

A blood vessel imaging system in accordance with a third embodiment of the present invention will be described with reference to FIG. 6, hereinbelow. In FIG. 6, a blood vessel imaging system in accordance with this embodiment comprises a first laser 111 emitting a first measuring light beam L1 at a wavelength λ1 of 760 nm, a second laser 112 emitting a second measuring light beam L2 at a wavelength λ2 of 930 nm, a first light heterodyne optical system 113 for the first measuring light beam L1, a second light heterodyne optical system 114 for the second measuring light beam L2, first and second photodetectors 115 and 116 which receive the first and second measuring light beams L1 and L2 emanating from the respective light heterodyne optical systems 113 and 114, a first signal detecting means 117 which is connected to the first photodetector 115 and detects the amplitude, due to the pulsation wave, of beat components which are included in the first measuring light beam L1 (more strictly the first combined light beam Lc1 to be described later) in the manner to be described later, and a second signal detecting means 118 which is connected to the second photodetector 116 and detects the amplitude, due to the pulsation wave, of beat components which are included in the second measuring light beam L2 (more strictly the second combined light beam Lc2 to be described later) in the manner to be described later.

The imaging system further comprises a personal computer (PC) 120 (as an image signal generating means) which receives outputs of the first and second signal detecting means 117 and 118, and an image monitor 121 such as a CRT display connected to the personal computer 120.

Further, there is provided a X-Y stage 123 which is movable in X and Y directions supporting thereon an object (e.g., a human finger) 122. A stage driver 124 drives the X-Y stage 123 under the control of the personal computer 120.

Figure 7:
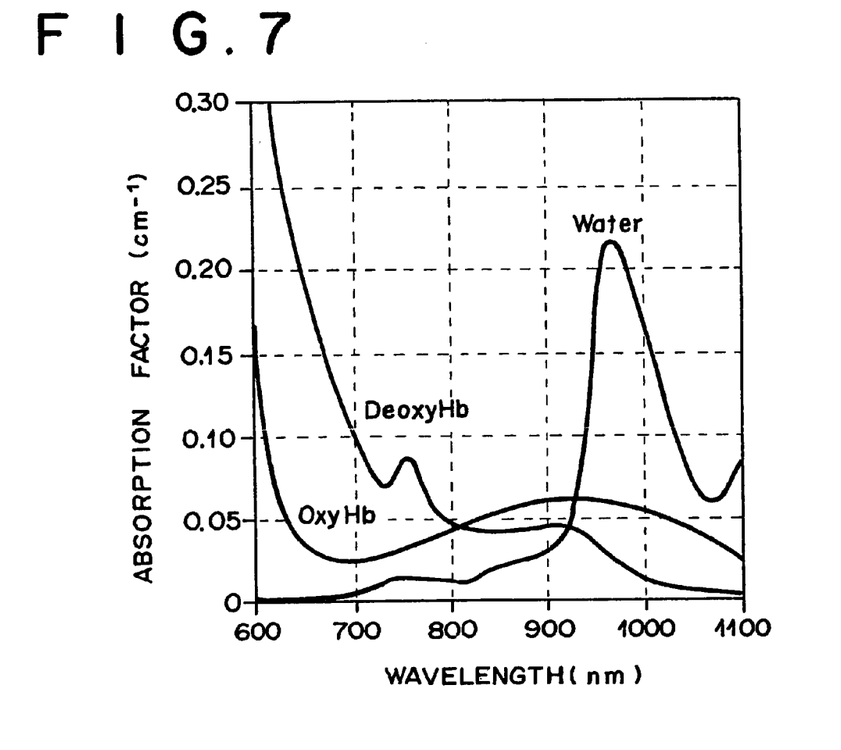
FIG. 7 is a graph showing absorption spectra of oxyhemoglobin, deoxyhemoglobin and water.

FIG. 7 shows absorption spectra of oxyhemoglobin (OxyHb) and deoxyhemoglobin (DeoxyHb), which are light absorbers in blood, together with an absorption spectrum of water, which governs optical characteristics of the tissue. As can be seen from FIG. 7, deoxyhemoglobin (DeoxyHb) is higher in absorbance than oxyhemoglobin (OxyHb) in a wavelength range lower than about 805 nm, where the former is equal to the latter in absorbance, and the latter is higher in absorbance than the former in a wavelength range higher than about 805 nm.

The wavelength λ1 of the first measuring light beam L1, 760 nm, is shorter than the "equi-absorption" wavelength 805 nm and deoxyhemoglobin is greatly higher than oxyhemoglobin in absorbance at 760 nm. On the other hand, the wavelength λ2 of the second measuring light beam L2, 930 nm, is longer than the "equi-absorption" wavelength 805 nm and oxyhemoglobin is greatly higher than deoxyhemoglobin in absorbance at 930 nm.

The first optical system 113, the first photodetector 115 and the first signal detecting means 117 form a first optical heterodyne detection system. The first optical system 113 comprises a half-silvered mirror 130 which splits the first measuring light beam L1 into a first section L11 (the part of the first measuring light beam L1 reflected by the half-silvered mirror 130) and a second section L12 (the part of the first measuring light beam L1 passing through the half-silvered mirror 130), a mirror 131 which reflects the first section L11 of the first measuring light beam L1 to impinge upon the object 122, a mirror 132 which reflects the second section L12 of the first measuring light beam L1, and a half-silvered mirror 133 which combines the first section L11 passing through the object 122 with the second section L12 reflected from the mirror 132 into a first combined light beam Lc1.

A frequency shifter 134 provided on the optical path of the second section L12 of the first measuring light beam L1 shifts the frequency of the second section L12 by a predetermined amount, e.g., several tens of MHz. The frequency shifter 134 may comprise, for instance, an AOM.

The second optical system 114, the second photodetector 116 and the second signal detecting means 118 form a second optical heterodyne detection system. The second optical system 114 comprises a half-silvered mirror 135 which splits the second measuring light beam L2 into a first section L21 (the part of the second measuring light beam L2 passing through the half-silvered mirror 130) and a second section L12 (the part of the second measuring light beam L2 reflected by the half-silvered mirror 135), a mirror 136 which reflects the first section L21 of the second measuring light beam L2, a dichroic mirror 137 which reflects the first section L21 of the second measuring light beam L2 reflected by the mirror 136 while permitting the first section L11 of the first measuring light beam L1 to pass through the dichroic mirror 137 so that the first sections L11 and L21 of the first and second measuring light beams L1 and L2 travel the same optical path to impinge upon the object 122, a pair of mirrors 138 and 139 which reflect in sequence the second section L22 of the second measuring light beam L2, a dichroic mirror 140 which reflects the first section L21 of the second measuring light beam L2 passing through the object 122 while permitting the first section L11 of the first measuring light beam L1 passing through the object 122 to pass through the dichroic mirror 140, thereby splitting the first sections L11 and L21 of the first and second measuring light beams L1 and L2 from each other, a mirror 141 which reflects the first section L21 of the second measuring light beam L2 reflected by the dichroic mirror 140, and a half-silvered mirror 142 which combines the first section L21 passing through the object 122 with the second section L22 reflected from the mirror 139 into a second combined light beam Lc2.

A frequency shifter 143 provided on the optical path of the second section L22 of the second measuring light beam L2 shifts the frequency of the second section L22 by a predetermined amount, e.g., several tens of MHz. The frequency shifter 143 may comprise, for instance, an AOM.

The half-silvered mirror 130 and the mirror 131 of the first optical system 113 and the half-silvered mirror 135, the mirror 136 and the dichroic mirror 137 of the second optical system 114 form an incident optical system which causes the first and second measuring light beams L1 and L2 to impinge upon the object 122 in the same position.

The first signal detecting means 117 comprises a band-pass filter 150 connected to the first photodetector 115, a level meter 151 connected to the band-pass filter 150, a band-pass filter 152 connected to the level meter 151, and a level meter 153 which is connected to the band-pass filter 152 and inputs an output signal into the personal computer 120.

The second signal detecting means 118 comprises a band-pass filter 154 connected to the second photodetector 116, a level meter 155 connected to the band-pass filter 154, a band-pass filter 156 connected to the level meter 155, and a level meter 157 which is connected to the band-pass filter 156 and inputs an output signal into the personal computer 120.

Operation of the blood vessel imaging system of this embodiment will be described, hereinbelow. When taking a blood vessel image, a first measuring light beam L1 (the first section L11) at 760 nm emitted from the first laser 111 and the second measuring light beam L2 (the first section L21) at 930 nm emitted from the second laser 112 are combined by the dichroic mirror 137 and are projected onto the object 122 in the same position. While projecting the measuring light beams L1 and L2, the X-Y stage 123 is moved in X and Y directions, whereby the first and second measuring light beams L1 and L2 caused to two-dimensionally scan the object 122.

Figure 8:
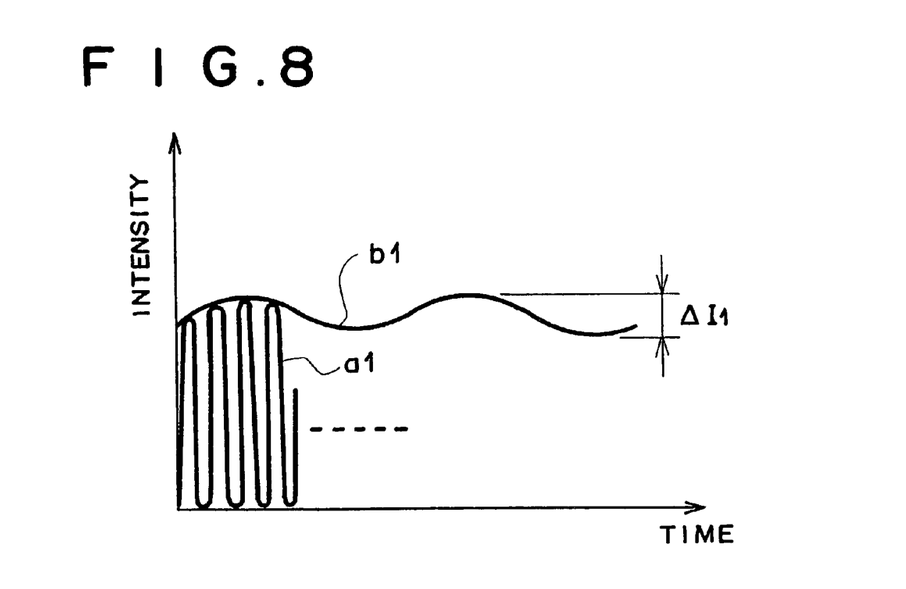
FIG. 8 is a view showing the waveform of the beat signal detected in the blood vessel imaging system of the third embodiment.

When the first section L11 of the first measuring light beam L1 passing through the object 122 is combined with the frequency-shifted second section L12 by the half-silvered mirror 133 into a first combined light beam Lc1, the first combined light beam Lc1 includes therein beat components whose frequency is equal to that of the frequency-shifted second section L12 of the first measuring light beam L1. The output of the first photodetector 115 upon receipt of the first combined light beam Lc1 includes a beat signal a1 generated by the beat components as shown in FIG. 8. When the first measuring light beam L1 passes through an artery part, the beat signal a1 is modulated at a frequency of about 1 Hz by the pulsation wave as shown by line b1 in FIG. 8.

The band-pass filter 150 connected to the first photodetector 115 transmits signal components in the band of the beat signal a1. The level meter 151 measures a level of the beat signal a1 passing through the band-pass filter 150. The output of the level meter 151 is input into the band-pass filter 152 and the band-pass filter 152 extracts the modulated components b1 (FIG. 8) at about 1 Hz. The level meter 153 measures an amplitude $\Delta I_1$ of the modulated components b1, and inputs a signal representing the amplitude $\Delta I_1$ into the personal computer 120.

When the first section L21 of the second measuring light beam L2 passing through the object 122 is combined with the frequency-shifted second section L22 by the half-silvered mirror 142 into a second combined light beam Lc2, the second combined light beam Lc2 includes therein beat components whose frequency is equal to that of the frequency-shifted second section L22 of the second measuring light beam L2. The output of the second photodetector 116 upon receipt of the second combined light beam Lc2 is similar to that of the first photodetector 115 shown in FIG. 8. The beat signal, the modulated components, and the amplitude of the modulated components based on the output of the second photodetector 116 are indicated at a2, b2 and $\Delta I_2$, hereinbelow.

The band-pass filter 154 connected to the second photodetector 116 transmits signal components in the band of the beat signal a2. The level meter 155 measures a level of the beat signal a2 passing through the band-pass filter 154. The output of the level meter 155 is input into the band-pass filter 156 and the band-pass filter 156 extracts the modulated components b2 at about 1 Hz. The level meter 157 measures an amplitude $\Delta I_2$ of the modulated components b2, and inputs a signal representing the amplitude $\Delta I_2$ into the personal computer 120.

The beat signal a1 output from the first photodetector 115 represents intensity of only straight light components traveling straight through the object 122, which is a scattering medium, or scattered light components close to the straight light components. Accordingly, by obtaining an image signal for the object 122 on the basis of the beat signal a1, a high spatial resolution can be ensured though the first measuring light beam L1 (the first section L11) is scattered by the object 122. This is also true for the second measuring light beam L2.

The first and second signal detecting means 117 and 118 output the amplitudes $\Delta I_1$ and $\Delta I_2$ for each scanning spot on the object 122 as the first and second measuring light beams L1 and L2 scan the object 122.

The personal computer 120 calculates the ratio $\log\Delta I_1/\log\Delta I_2$ of logarithmic values of the amplitudes $\Delta I_1$ and $\Delta I_2$. The value of the ratio $\log\Delta I_1/\log\Delta I_2$ corresponds to the value of the degree of oxygen saturation of the blood as described above. The personal computer 120 generates an image signal component Sp bearing thereon a relatively high density (low brightness) when the degree of oxygen saturation represented by the ratio $\log\Delta I_1/\log\Delta I_2$ is 80 to 90% and generates an image signal component Sp bearing thereon a relatively low density (high brightness) when the degree of oxygen saturation represented by the ratio $\log\Delta I_1/\log\Delta I_2$ is not in the range of 80 to 90%.

The image monitor 121 reproduces a two-dimensional image on the basis of an image signal made up of the image signal components Sp thus generated for the respective scanning spots. In the image, only the artery part of the object 22 is shown.

The reason why the ratio $\log\Delta I_1/\log\Delta I_2$ corresponds in one-to-one correspondence to the degree of oxygen saturation will be described, hereinbelow. The change in the amplitude $\Delta I_1$ shown in FIG. 8 is caused by change in volume in response to pulsation of arterial blood. When the concentration of hemoglobin is represented by C, the absorption factor of hemoglobin to a wavelength of 760 nm is represented by $E_1$ and the amount of change of the optical path through the artery part is represented by $\Delta D$, $\log\Delta I_1 = E_1 \cdot C \cdot \Delta D$. Similarly When the absorption factor of hemoglobin to a wavelength of 930 nm is represented by $E_2$, $\log\Delta I_2 = E_2 \cdot C \cdot \Delta D$. Accordingly, $\log\Delta I_1/\log\Delta I_2 = E_1/E_2$. Further since the absorption factors $E_1$ and $E_2$ correspond to the degree of oxygen saturation, the ratio $\log\Delta I_1/\log\Delta I_2$ corresponds to the degree of oxygen saturation.

Figure 9:
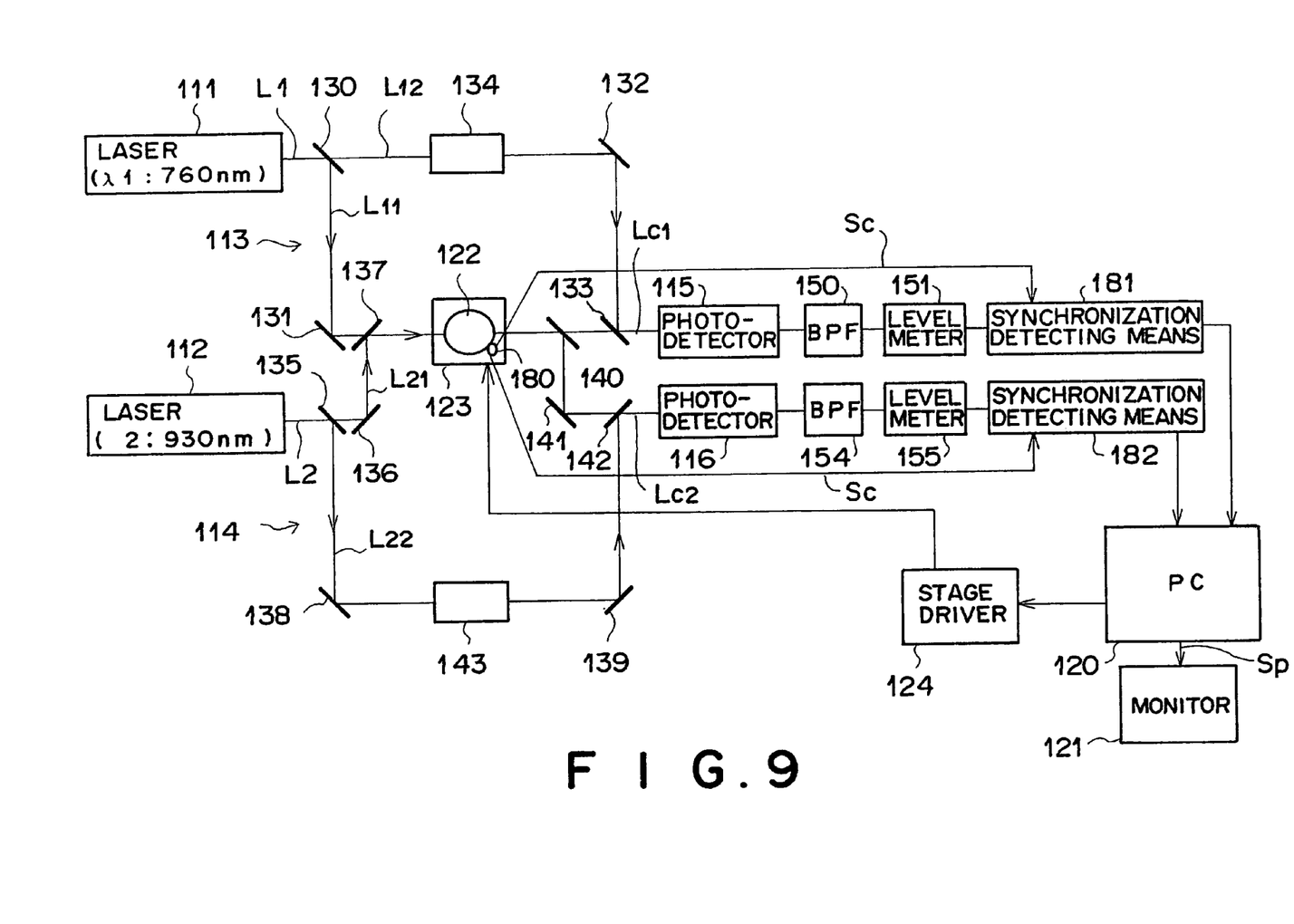
FIG. 9 is a schematic view showing a blood vessel imaging system in accordance with a fourth embodiment of the present invention.

A blood vessel imaging system in accordance with a fourth embodiment of the present invention will be described with reference to FIG. 9, hereinbelow. In FIG. 9, the elements analogous to those shown in FIG. 6 are given the same reference numerals and will not be described here.

The blood vessel imaging system of this embodiment basically differs from that of the first embodiment in that there is added a system which detects levels of the beat signals a1 and a2 in synchronization with a pulsation wave of the object 122. That is, there are provided a synchronization detecting means 181 in place of the band-pass filter 152 and the level meter 153 and a synchronization detecting means 182 in place of the band-pass filter 156 and the level meter 157, and there is further provided a pulsation signal detecting means 180 such as an electrocardiograph which detects a pulsation wave of the object 122.

The pulsation signal detecting means 180 inputs a pulsation wave signal Sc into the synchronization detecting means 181 and 182. The synchronization detecting means 181 samples the output signal of the level meter 151 in synchronization with the peak and the bottom of the pulsation wave of the object 122 represented by the pulsation wave signal Sc, and the difference between the levels of the sampled two signals, that is, the amplitude $\Delta_1$ of the pulsation wave is obtained. Similarly, the synchronization detecting means 182 samples the output signal of the level meter 153 in synchronization with the peak and the bottom of the pulsation wave of the object 122 represented by the pulsation wave signal Sc, and the difference between the levels of the sampled two signals, that is, the amplitude $\Delta I_2$ of the pulsation wave is obtained.

The personal computer 120 generates an image signal component on the basis of the amplitudes $\Delta I_1$ and $\Delta I_2$.

In cases where the system of one of the first, second, third, and fourth embodiments described above is employed, the spatial distribution of the pulsation wave signal can be determined. Specifically, for example, in the system of the first embodiment, the peak value Ip of the signal in the pulsation wave band near 1 Hz and the intensity ratio Ip/Ib may be calculated by the personal computer 20 with respect to two or more different points on the object 22. In this manner, the spatial distribution of the pulsation wave signal generated by the pulsation wave of the artery can be determined.

Also, in the system of the second embodiment, the degree of modulation of the beat signal {IF(H)−IF(L)}/{IF(H)+IF(L)} may be calculated by the personal computer 20 with respect to two or more different points on the object 22. In this manner, the spatial distribution of the pulsation wave signal generated by the pulsation wave of the artery can be determined.

Further, in the system of the third embodiment or the fourth embodiment, the ratio $\log\Delta I_1/\log\Delta I_2$ of the logarithmic values of the amplitudes $\Delta I_1$ and $\Delta I_2$ may be calculated by the personal computer 120 with respect to two or more different points on the object 122. In this manner, the spatial distribution of the pulsation wave signal generated by the pulsation wave of the artery can be determined.

What is claimed is:

1. A blood vessel imaging system comprising
   a measuring light source which emits a measuring light beam,
   a scanning means which causes the measuring light beam to scan an organism,
   an optical heterodyne detection system consisting of an optical system which splits the measuring light beam upstream of the organism into a first light beam traveling to impinge upon the organism and a second light beam traveling not to impinge upon the organism and combines the second light beam with the first beam emanating from the organism into a combined light beam, a frequency shifter which causes the first and second light beams to have frequencies different from each other, and a beat component detecting means which detects beat components of the combined light beam, and
   an image signal generating means which generates an image signal on the basis of the ratio of the intensity of a pulsation wave band signal to the intensity of a beat signal included in an output signal of the optical heterodyne detection system.

2. A blood vessel imaging system as defined in claim 1 in which
there is provided a frequency analysis means which analyzes the output signal of the optical heterodyne detection system, and
the image signal generating means obtains the intensity ratio on the basis of the pulsation wave band signal and the beat signal separated from each other by the frequency analysis means on a frequency axis.

3. A blood vessel imaging system as defined in claim 1 or 2 in which the image signal generating means generates an image signal representing artery parts of the organism when the intensity ratio is higher than a predetermined threshold level.

4. A blood vessel imaging system as defined in claim 1 or 2 in which the measuring light source comprises a linear or two-dimensional array of a plurality of light emitting portions, the optical heterodyne detection system is arranged to be able to detect in parallel beat components of the combined light beams based on the measuring light beams from the respective light emitting portions, and the measuring light source and the optical heterodyne detection system also function as at least a part of said scanning means.

5. A blood vessel imaging system comprising
a measuring light source which emits a measuring light beam,
a scanning means which causes the measuring light beam to scan an organism,
an optical heterodyne detection system consisting of an optical system which splits the measuring light beam upstream of the organism into a first light beam traveling to impinge upon the organism and a second light beam traveling not to impinge upon the organism and combines the second light beam with the first beam emanating from the organism into a combined light beam, a frequency shifter which causes the first and second light beams to have frequencies different from each other, and a beat component detecting means which detects beat components of the combined light beam, and
an image signal generating means which generates an image signal on the basis of the degree of modulation at a pulsation wave band frequency of a beat signal included in an output signal of the optical heterodyne detection system.

6. A blood vessel imaging system as defined in claim 5 in which there is provided a pulsation wave detecting means which detects a pulsation wave of the organism, and the image signal generating means samples the signal value when the beat signal is in a predetermined phase on the basis of an output signal of the pulsation wave detecting means.

7. A blood vessel imaging system as defined in claim 5 or 6 in which the image signal generating means generates an image signal representing artery parts of the organism when the degree of modulation is higher than a predetermined threshold level.

8. A blood vessel imaging system as defined in claim 5 or 6 in which the measuring light source comprises a linear or two-dimensional array of a plurality of light emitting portions, the optical heterodyne detection system is arranged to be able to detect in parallel beat components of the combined light beams based on the measuring light beams from the respective light emitting portions, and the measuring light source and the optical heterodyne detection system also function as at least a part of said scanning means.

9. A blood vessel imaging system comprising
a measuring light source which emits first and second measuring light beams which are different in frequency,
an incident optical system which causes the first and second measuring light beams to impinge upon the organism in the same position,
a scanning means which causes the first and second measuring light beams to scan an organism,
a first optical heterodyne detection system consisting of an optical system which splits the first measuring light beam upstream of the organism into a first section traveling to impinge upon the organism and a second section traveling not to impinge upon the organism and combines the second section with the first section emanating from the organism into a first combined light beam, a frequency shifter which causes the first and second sections of the first light beam to have frequencies different from each other, and a beat component detecting means which detects beat components of the first combined light beam,
a second optical heterodyne detection system consisting of an optical system which splits the second measuring light beam upstream of the organism into a first section traveling to impinge upon the organism and a second section traveling not to impinge upon the organism and combines the second section with the first section emanating from the organism into a second combined light beam, a frequency shifter which causes the first and second sections of the second light beam to have frequencies different from each other, and a beat component detecting means which detects beat components of the second combined light beam, and
an image signal generating means which calculates characteristic value in one-to-one correspondence to a degree of oxygen saturation on the basis of beat component detection signals respectively output from the first and second optical heterodyne detection systems, and generates an image signal on the basis of the characteristic value.

10. A blood vessel imaging system as defined in claim 9 in which the image signal generating means generates an image signal employing, as the characteristic value, the ratio between a logarithm of amplitude of the beat component detection signal output from the first optical heterodyne detection system due to a pulsation wave of the organism and a logarithm of amplitude of the beat component detection signal output from the second optical heterodyne detection system due to the pulsation wave of the organism.

11. A blood vessel imaging system as defined in claim 10 in which
there are provided a filtering means which extracts modulated components at frequencies in the pulsation wave bands out of the beat component detection signals respectively output from the first and second optical heterodyne detection systems, and a level meter which measures levels of the signals extracted by the filtering means, and
the image signal generating means obtains the amplitudes due to the pulsation wave on the basis of output signals of the level meter.

12. A blood vessel imaging system as defined in claim 10 in which
there are provided a pulsation wave detecting means which detects a pulsation wave output from the organism, and
a sampling means which samples the beat component detection signals respectively output from the first and second optical heterodyne detection systems at timings at which the beat component detection signals are maximized and minimized on the basis of an output signal of the pulsation wave detecting means may be provided, and the image signal generating means obtains the amplitudes due to the pulsation wave on the basis of the sampled values of beat components detection signals.

13. A blood vessel imaging system as defined in claim 9, 10, 11, or 12 in which the first and second measuring light beams are 760 nm and 930 nm in frequency, respectively.

14. A blood vessel imaging system as defined in claim 9, 10, 11, or 12 in which the image signal generating means outputs an image signal representing an artery part of the organism when it calculates said characteristic value to be a value corresponding to a degree of oxygen saturation of 80 to 90%.

15. A blood vessel imaging system as defined in claim 9, 10, 11, or 12 in which the measuring light source comprises first and second linear or two-dimensional arrays of a plurality of light emitting portions, the light emitting portions of the first array emitting a plurality of first measuring light beams and the light emitting portions of the second array emitting a plurality of second measuring light beams, the first optical heterodyne detection system is arranged to be able to detect in parallel beat components of the first combined light beams based on the first measuring light beams from the respective light emitting portions, the second optical heterodyne detection system is arranged to be able to detect in parallel beat components of the second combined light beams based on the second measuring light beams from the respective light emitting portions, and the measuring light source and the optical heterodyne detection systems also function as at least a part of said scanning means.

16. A system for determining a spatial distribution of a pulsation wave signal, comprising a measuring light source which emits a measuring light beam impinging upon an organism, an optical heterodyne detection system consisting of an optical system which splits the measuring light beam upstream of the organism into a first light beam traveling to impinge upon the organism and a second light beam traveling not to impinge upon the organism and combines the second light beam with the first beam emanating from the organism into a combined light beam, a frequency shifter which causes the first and second light beams to have frequencies different from each other, and a beat component detecting means which detects beat components of the combined light beam, and a pulsation wave signal generating means for generating a pulsation wave signal, which represents a pulsation wave of the organism, on the basis of an output signal of the optical heterodyne detection system.

17. A system for determining a spatial distribution of a pulsation wave signal as defined in claim 16 in which the pulsation wave signal generating means is a means for generating the pulsation wave signal on the basis of the ratio of the intensity of a pulsation wave band signal to the intensity of a beat signal included in the output signal of the optical heterodyne detection system.

18. A system for determining a spatial distribution of a pulsation wave signal as defined in claim 17 in which the pulsation wave signal generating means generates a pulsation wave signal representing a pulsation wave of an artery of the organism when the intensity ratio is higher than a predetermined threshold level.

19. A system for determining a spatial distribution of a pulsation wave signal as defined in claim 16 in which the pulsation wave signal generating means is a means for generating the pulsation wave signal on the basis of the degree of modulation at a pulsation wave band frequency of the beat signal included in the output signal of the optical heterodyne detection system.

20. A system for determining a spatial distribution of a pulsation wave signal as defined in claim 19 in which the pulsation wave signal generating means generates a pulsation wave signal representing a pulsation wave of an artery of the organism when the degree of modulation is higher than a predetermined threshold level.

21. A system for determining a spatial distribution of a pulsation wave signal, comprising a measuring light source which emits first and second measuring light beams which are different in frequency, an incident optical system which causes the first and second measuring light beams to impinge upon the organism in the same position, a scanning means which causes the first and second measuring light beams to scan an organism, a first optical heterodyne detection system consisting of an optical system which splits the first measuring light beam upstream of the organism into a first section traveling to impinge upon the organism and a second section traveling not to impinge upon the organism and combines the second section with the first section emanating from the organism into a first combined light beam, a frequency shifter which causes the first and second sections of the first light beam to have frequencies different from each other, and a beat component detecting means which detects beat components of the first combined light beam, a second optical heterodyne detection system consisting of an optical system which splits the second measuring light beam upstream of the organism into a first section traveling to impinge upon the organism and a second section traveling not to impinge upon the organism and combines the second section with the first section emanating from the organism into a second combined light beam, a frequency shifter which causes the first and second sections of the second light beam to have frequencies different from each other, and a beat component detecting means which detects beat components of the second combined light beam, and a pulsation wave signal generating means which calculates characteristic value in one-to-one correspondence to a degree of oxygen saturation on the basis of beat component detection signals respectively output from the first and second optical heterodyne detection systems, and generates a pulsation wave signal on the basis of the characteristic value.

22. A system for determining a spatial distribution of a pulsation wave signal as defined in claim 21 in which the pulsation wave signal generating means generates the pulsation wave signal by employing, as the characteristic value, the ratio between a logarithm of amplitude of the beat component detection signal output from the first optical heterodyne detection system due to a pulsation wave of the organism and a logarithm of amplitude of the beat component detection signal output from the second optical heterodyne detection system due to the pulsation wave of the organism.

23. A system for determining a spatial distribution of a pulsation wave signal as defined in claim 21 in which a wavelength $\lambda 1$ of the first measuring light beam falls within the range of 600 nm<$\lambda 1$<805 nm, and a wavelength $\lambda 2$ of the second measuring light beam falls within the range of 805 nm<$\lambda 2$<1,100 nm.

24. A system for determining a spatial distribution of a pulsation wave signal as defined in claim 23 in which the wavelength $\lambda 1$ of the first measuring light beam is 760 nm, and the wavelength $\lambda 2$ of the second measuring light beam is 930 nm.

25. A method of determining a spatial distribution of a pulsation wave signal, comprising the steps of obtaining a pulsation wave signal by utilizing a system for determining a spatial distribution of a pulsation wave signal as defined in any of claims 16 to 24.

26. A method of determining a spatial distribution of a pulsation wave signal as defined in claim 25 in which the pulsation wave signal is obtained with respect to at least two different points on the organism.

* * * * *